United States Patent
Parekh et al.

(10) Patent No.: US 7,360,394 B2
(45) Date of Patent: Apr. 22, 2008

(54) MULTI-PURPOSE MODULAR PYROLYSIS AND THERMAL PROCESSING SYSTEM FOR CHEMICAL AND BIOLOGICAL THREAT AGENT DETECTION

(76) Inventors: Dhirajlal G. Parekh, 9 Westspring Way, Lutherville, MD (US) 21093; Waleed Maswadeh, 8923 Philadelphia Rd., Rosedale, MD (US) 21237; Amit Limaye, 59 Grasmere Way, Princeton, NJ (US) 08540

( * ) Notice: Subject to any disclaimer, the term of this patent is extended or adjusted under 35 U.S.C. 154(b) by 49 days.

(21) Appl. No.: 11/196,490

(22) Filed: Aug. 3, 2005

(65) Prior Publication Data
US 2008/0053192 A1 Mar. 6, 2008

Related U.S. Application Data

(60) Provisional application No. 60/598,389, filed on Aug. 3, 2004.

(51) Int. Cl.
*G01N 30/16* (2006.01)
*G01N 30/62* (2006.01)

(52) U.S. Cl. ............... 73/23.35; 73/23.41; 73/23.42; 95/82; 95/89; 96/101; 96/105; 422/89

(58) Field of Classification Search ............... 73/23.35, 73/23.41, 23.42; 95/82, 89; 96/101, 105; 422/89
See application file for complete search history.

(56) References Cited

U.S. PATENT DOCUMENTS 5,394,733 A * 3/1995 Acholla ............... 73/23.41
5,527,507 A * 6/1996 Childers et al. ............... 422/28

* cited by examiner

*Primary Examiner*—Daniel S. Larkin
(74) *Attorney, Agent, or Firm*—Ober/Kaler; Royal W. Craig

(57) ABSTRACT

A multi-purpose modular pyrolysis and thermal processing system (MPMPTPS) for pyrolyzing and/or vaporizing liquids and solids to create an evolved vapor suitable for introduction into a gas-chromatography and/or vapor detection system, thereby allowing detection, classification and/or identification characteristics of threat agents. The MPMPTPS system is capable of pyrolyzing and/or vaporizing liquid (in solution, suspension or colloidal form) and solid (in aerosol or powder form) form of biological and chemical threat agents in a manner that the evolved vapor may be introduced into Gas-Chromatography systems and/or vapor detection systems, without the use of any reagents and/or bottled gases.

2 Claims, 5 Drawing Sheets

Open port inlet for aerosol concentrator
liquid suspensions and colloids,
solid samples, mist and chemical vapors. (1)

FSV-1   FSV-2   P1

Filter Clean-out
Cross Flow 100 ml/min

Filter Clean-out
Flow > 1000 ml/min

FAV-2
16
18
14
FSV-6

Aerosol collection flow: >500 ml/min

Open port pyrolysis and
thermal vaporization unit

P2
FAV-1

12
Drying flow: 10-15 ml/min

20
Filter Clean-out
Flow > 1000 ml/min

FSV-4

Carrier Gas flow
Application dependent 22
68   62   64

FSV-5

SPME and
Clear Liquid
Injection Port

66

FSV-7

P3
6

Split or vent flow
Application dependent

FSV = Flow switching valve

To Gas Chromatograph
or
Detector

FIG. 1

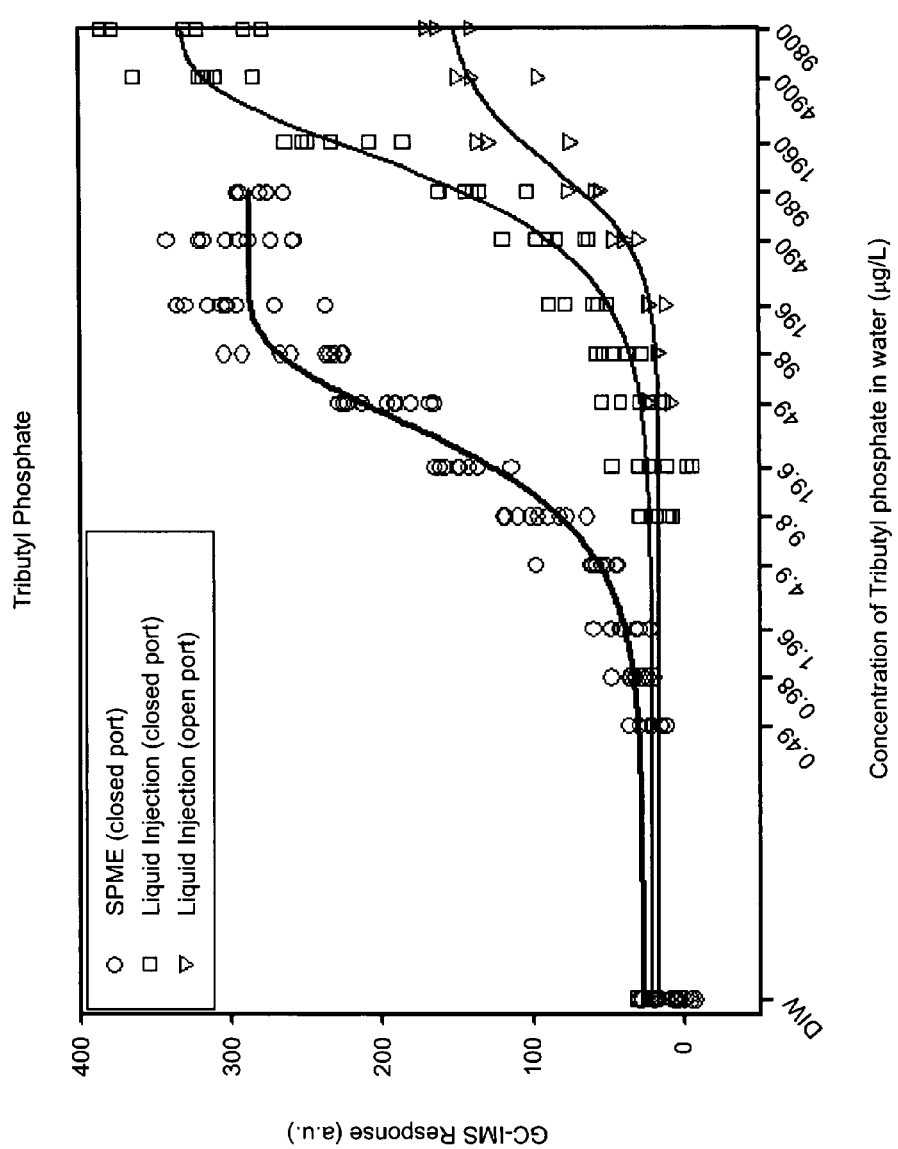
FIG. 5 Comparison of closed port and open port liquid chemical anaylsis

MULTI-PURPOSE MODULAR PYROLYSIS AND THERMAL PROCESSING SYSTEM FOR CHEMICAL AND BIOLOGICAL THREAT AGENT DETECTION

CROSS-REFERENCE TO RELATED APPLICATIONS

The present application derives priority from U.S. Provisional Patent Application No. 60/598,389 filed Aug. 3, 2004.

BACKGROUND OF INVENTION

1. Field of Invention

The present invention relates to systems for pyrolyzing (thermally decomposing) and/or vaporizing liquid (in solution, suspension or colloidal form) and solid (in aerosol or powder form) form of biological and chemical threat agents in a manner that the evolved vapor may be introduced into Gas-Chromatography systems, vapor detection systems, and Solid Phase Micro Extraction (SPME) systems, without the use of any reagents and/or bottled gases, for analysis of the evolved vapors and detection, classification and/or identification characteristics of the analyzed threat agent.

2. Brief Description of Related Art

The threat of biological and chemical threat agent attacks looms large in the world today. The first step in meeting this threat is the ability to detect the release of biological and chemical threat agents. Early detection and counter measures have become a high priority in many military, government and private laboratories. Many chemical warfare (CW) and biological warfare (BW) agents are difficult to detect using conventional staining techniques. Consequently, various other approaches have been developed such as Pyrolysis/Mass Spectrometry and Pyrolysis-Gas Chromatography-Ion Mobility Spectrometry (Py-GC/IMS).

Pyrolysis is a form of thermally driven process that chemically decomposes organic materials by heat. Pyrolysis typically occurs under pressure and at operating temperatures above 430° C. (800° F.). Large organic molecules are decomposed into smaller molecular weight moieties occasionally leaving a solid residue containing carbon and ash. Pyrolysis is widely used for waste disposal, and is becoming a viable way of characterizing organic threat agents as well. For example, the Block II Chemical Biological Mass Spectrometer (CBMS) is a developmental instrument for point detection that integrates the detection and identification of both CW and BW agents into a single compact unit. It is based upon a direct-sampling ion trap mass spectrometer. After collection of a sample, a pyrolyzer body heater is heated to pyrolize the sample. K. J. Hart, M. B. Wise, W. H. Griest, and S. A. Lammert, "Design, Development and Performance of a Fieldable Chemical & Biological Agent Detector," Field Analytical Chemistry and Technology, 4 (22-3), 93-110 (2000). However, this and other commercially available Chemical Biological Mass detectors are capable only of detecting CW and BW agents in vapor samples. It would be far more advantageous to add the capability of detecting CW/BW agents in liquids and solids as well, thereby providing a universal threat analysis system suitable for use with solids, aerosols, liquid solutions, liquid suspensions, liquid colloids, mists and vapors. A fully-functioning field-able thermal analyses based sample-processing system for these multiple sample forms would greatly increase the versatility and market-based demand, especially for the purpose of chemical and biological threat assessment.

SUMMARY OF THE INVENTION

It is, therefore, an object of the present invention to provide a universal threat analysis system suitable for use with solids, aerosols, liquid solutions, liquid suspensions, liquid colloids, mists and vapors.

It is another object to provide a fully-functioning field-able thermal analyses based sample-processing system for these multiple sample forms to increase versatility and market-based demand, especially for the purpose of chemical and biological threat assessment.

It is another object to provide an apparatus for pyrolyzing (thermally decomposing) and/or vaporizing liquids (in solution, suspension or colloidal form) and solids (in aerosol or powder form) to create an evolved vapor suitable for introduction into a variety of gas-chromatography and/or vapor detection systems, thereby allowing detection, classification and/or identification characteristics of threat agents.

The foregoing and other objects are accomplished by providing a multi-purpose and modular pyrolysis and thermal processing system (MPMPTPS) for pyrolyzing and/or vaporizing liquids and solids to create an evolved vapor suitable for introduction into a gas-chromatography and/or vapor detection system, thereby allowing detection, classification and/or identification characteristics of threat agents. The present system adds the capability of liquid and solid phase analysis to existing commercially available vapors-only detection systems. By incorporating the MPMPTPS to the chemical-vapors-only detectors, a multi-purpose field-able biological threat analysis system can be readily manufactured for the purpose of chemical and biological threat assessment. Any threat agent can be analyzed, whether in solid, aerosol, liquid solution, liquid suspension, liquid colloid, mist or vapor form. This greatly increases the versatility and market-based desirability of commercially-available chemical-vapors-only detectors.

The device generally comprises two inlet ports. The first inlet port is open-to-ambient-atmosphere and pyrolysis based. The sample is collected in aerosol, solid, liquid suspension, liquid colloid, mist and/or ambient vapor form. If the sample is in aerosol, solid, liquid suspension, liquid colloid and/or mist form, the sample is retained on a quartz filter located inside the pyrolyzer device. The sample is rapidly heated to release characteristic pyrolyzate and/or vapors. These vapors can be analyzed either first by using a gas chromatography (GC) based separation technique to separate the pyrolyzate into its individual chemical components, and then analyzing the separated components with a chemical-vapors-only detector; or directly injecting the pyrolyzate and/or vapors into a chemical-vapors-only detector. The second port is the split-less closed GC-injector type interface. This port allows for the entry of analyte in the form of clear liquid injection and Solid-Phase Micro Extractor (SPME) loaded with the chemical analyte. Though the closed port can be used for biological analyses, it is better suited to analyze liquid chemical samples.

DETAILED DESCRIPTION

The purpose of the MPMPTPS is to be able to collect a sample in aerosol form (using any air to air aerosol concentrator with minor flows of up to 2 liter/min and depositing the concentrated aerosol on to the pyrolysis region), solid form (by directly depositing the solid sample on the pyrolysis region), liquid suspension, colloids and/or solutions (by direct liquid injections of up to 2 μl aliquots on to the pyrolysis region) and vapor form.

The device generally comprises two inlet ports: an "open port" and a "closed port". The open inlet port is open-to-ambient-atmosphere and pyrolysis based. The sample is collected in aerosol, solid, liquid suspension, liquid colloid, mist and/or ambient vapor form. If the sample is in aerosol, solid, liquid suspension, liquid colloid and/or mist form, the sample is retained on a quartz filter located inside the pyrolyzer device. The sample is rapidly heated to release characteristic pyrolyzate and/or vapors. These vapors can be analyzed by either first by using a gas chromatography (GC) based separation technique to separate the pyrolyzate into its individual chemical components and then analyzing the separated components with a chemical-vapors-only detector or directly injecting the pyrolyzate and/or vapors into a chemical-vapors-only detector. The closed port is a split-less closed GC-injector type interface. This port allows for the entry of analyte in the form of clear liquid injection and Solid-Phase Micro Extractor (SPME) loaded with the chemical analyte. Though the closed port can be used for biological analyses, it is better suited to analyze liquid chemical samples.

Biological samples, chemical samples in colloidal or suspension form and vapors are analyzed using the open port only. The clear liquid chemical samples can be analyzed using the closed port, which gives better sensitivity than the open port option. For additional and more detailed chemical analysis, the SPME option can be utilized using the closed port option.

The pyrolysis of biological substances is achieved by heating the biological sample from 100 C (dry sample) to 500 C in less than seven seconds. The pyrolysis decomposes the solid biological sample into representative gaseous products, which reveal the classification and/or identification characteristics of the analyzed sample. The thermal vaporization of chemical (both in open and closed port) can be achieved by simply heating the sample to 300 C, as is done in-lab chemical analyses.

As will be described, the MPMPTPS system is also equipped with a self-clean-out filter mode. A clean filter prolongs the aerosol analysis time to a minimum of twenty-four hours of uninterrupted aerosol interrogation. The above described components are described in detail below.

Components of the MPMPTPS System

The various components that form the MPMPTPS system are described in detail in the subsequent paragraphs.

FIG. 1 is a schematic diagram of a preferred embodiment of the MPMPTPS system 2. The open port pyrolysis and thermal vaporization unit 4 is used for solids, liquids and vapor analysis. However, for clear liquids chemical analysis, the closed port 6 should be used.

FIG. 5 shows a graphical comparative analysis of tri-butyl phosphate (TBP) dissolved in water.

OPEN PORT PYROLYSIS AND THERMAL VAPORIZATION UNIT 4

Figure 2:
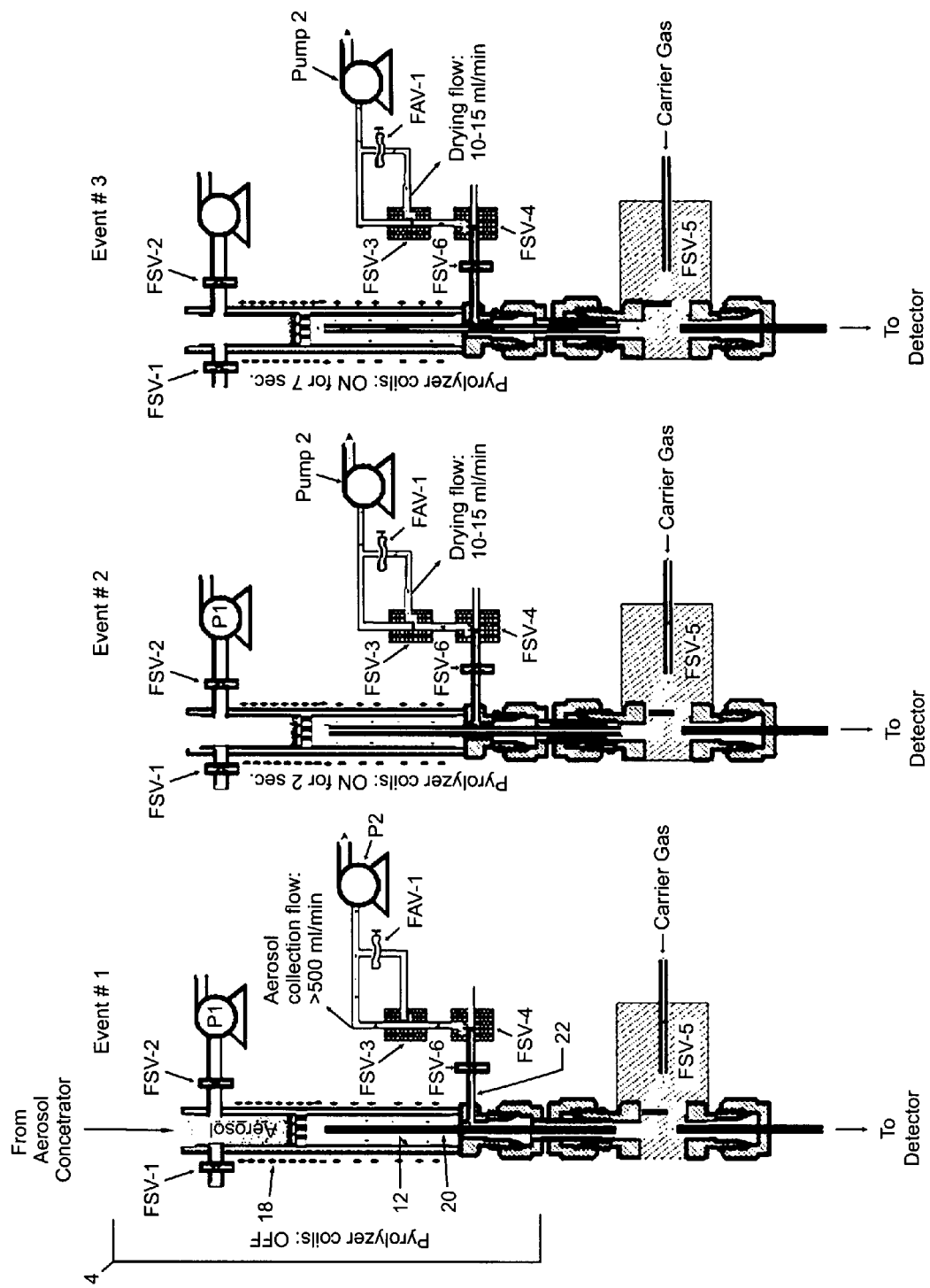
FIG. 2 is a sequential diagram illustrating the event sequence for performing the biological analysis, which include sample collection, drying and pyrolysis.

The open port unit 4 is made up of a standard fritted Gas Chromatograph capillary inlet liner 12. Pyrex or quartz tube is the preferred choice because of the high temperature resilience. The injector liner 12 must be equipped with a quartz frit 14 of thickness less than 3 mm. The length of the inlet liner 12 should be 40-60 mm long, between 3-5 mm in inner diameter with the tube wall thickness of 1-1.5 mm. The frit 14 should be placed in the mid-point along the length of the inlet liner 12. The frit 14 serves as the back-support for filter paper 16 that is used to trap aerosol particles in the pyrolysis region. Whatman QMA-100 filter paper is an appropriate filter paper for the purpose of trapping and subsequent pyrolysis of aerosol particles. The filter paper 16 preferably has a 0.5 μm pore size and can withstand temperatures of up to 500 C. Also, this filter 16 should be capable of trapping PM-10 aerosol. A length of the inlet liner 12 is wrapped with pyrolyzer heating coils 18, which may be NiChrome wire. The heating coils 18 must be capable of heating the collected aerosol sample from 100 C to 500 C in less than seven seconds. This can be achieved by passing a four (4) ampere DC current driven by 15 Volts through a 575 to 625 mm long 0.33 mm OD NiChrome wire 18. This wire 18 is coiled around the pyrolyzer inlet liner 12 in two distinct coiling densities. The first density (shown by close-cropped dotted lines) is calculated to achieve pyrolysis, and is approximately two coils per millimeter along the length of the inlet liner 12 (covering the external surface of the pyrolyzer inlet liner 12), thereby defining the pyrolysis region. This first pyrolysis coiling density should be utilized 2 mm downstream of the frit 14, along the frit 14 and 4 mm upstream of the frit 14, totaling 8 mm, which entirely covers the frit 14. This first coiling density will ensure that the pyrolyzer region will be heated from 100 C to 500 C in less than seven seconds. The second coiling density (shown by spaced dotted lines) is the heated tube coiling density. This density is preferably about 0.5 coils per millimeter. The purpose of the heated tube coil density is to heat the downstream portion of the pyrolyzer inlet liner 12 to about 150-200 C. This temperature in the range of 150 to 200 C ensures that the pyrolyzate that is generated in the pyrolyzer region does not condense to the walls of the pyrolyzer inlet liner 12 in the downstream portion from the frit 14. A 30 mm long, 0.535 mm inner diameter deactivated silico-steel transfer line 20 is used to transport the pyrolyzate via a heated three-way valve FSV-5 to the detector unit. The transfer-line 20 opening is kept at a distance of 1.5 to 2.5 mm from the downstream end of the frit 14. This distance is found optimum for transport of the generated vapors without drastic dilution and maximum capture of the vapors. Under the "normally closed" setting, the FSV-5 valve is closed to the flow from the open port. The aerosol is collected by a pump P2, which is pneumatically connected to the pyrolyzer inlet liner 12 via another transfer line 22. The aerosol collection flow transfer line 22 should be at least a 2 mm inner diameter steel tube. The aerosol collection flow transfer line 22 is connected to a non-heated three-way valve FSV-4 which, under a "normally closed" position, allows for the aerosol collection transfer line 22 to be pneumatically connected to another non-heated three-way valve FSV-3. This valve FSV-3 in its "normally closed" position allows the aerosol collection pump P2 to pull 500 ml/min or more flow of air through the pyrolyzer inlet liner 12, thereby allowing aerosol to be collected on the filter paper 16.

Closed Port Thermal Vaporization Unit 6

The closed port option is designed primarily for clear liquid and SPME based chemical analyses. The closed port unit 6 is comprised of a frit-less and split-less standard deactivated gas chromatograph injector liner 62. The liner 62 is wrapped along its length with heating coils 64, which may be coiled 600 mm long, 0.33 outer diameter NiChrome heating wire. The heating wire coil density is uniform along the length of the liner 62. The heating wire 64 is constantly supplied with 15 VDC current of enough magnitude to maintain the injector liner 62 at about 130 C. As soon as the sample is injected, the amount of 15 VDC current is stepped up to drive the temperature inside the liner 62 from 130 C to about 400-450 C in less than seven seconds. This can be achieved by passing a 4 amp DC current driven by 15 Volts.

The temperature of 400-450 C is enough to vaporize almost all of the chemical threat agents. Although not primarily designed for biological analyses, the temperature of 400-450 C is also sufficient to pyrolyze biological samples as well. A user selected carrier gas flow is maintained through the liner 62. The user must adjust the carrier gas flow rate according to the detector and experimental needs. The sample input end of the liner 62 is sealed with a high temperature low-volatility septum 66, such as THERMOLITE™ septa from Restek corporation. The septum 66 allows for injection of liquid with the help of a sharp needle syringe and also SPME analyses, without allowing for loss of generated vapors to the ambient atmosphere. The detainment of almost all of the generated vapors improves the limit of detection, which is vital for successful commercialization. The generated vapors are transported for analysis via the transfer line 68, which may be a 30 mm long, 0.535 mm inner diameter deactivated silico-steel transfer line into a flow-switching three-way valve FSV-5. Valve FSV-5 is open to the closed port under its "normally closed" setting.

Flow Switching Valves and Pumps

To incorporate the multi-mode thermal analysis in a completely modular and self-contained package, a set of flow switching valves (FSV-1 . . . n), flow adjustment valves (FAV-1 . . . n) and pumps (P1 . . . n) are employed. The on-off valves FSV-1 and FSV-2 are used to self-clean the filter paper 16 during prolonged aerosol analysis mode. The valve FAV-1 is used to adjust the drying cross flow. The on-off valve FSV-6 allows the aerosol collection and filter 16 self-clean mode to be pneumatically connected to the pyrolyzer inlet liner 12. The three-way valve FSV-3 is used for switching the flow between aerosol collection and solid drying flow. The flow adjustment valve FAV-1 is used to set the drying flow rate in a 10-15 ml/min range. The three-way valve FSV-4 is used to switch flows between aerosol collection mode and filter self-clean mode. The on-off valve FSV-7 is used to initiate the split mode, if the split-less mode of gas chromatograph-injection is not desirable due to high analyte load. The flow switching valves FSV-1, FSV-2, FSV-3, FSV-4, FSV-6 and FSV-7 may all be commercially-available gas millivolt switching valves capable of operating at room temperature such as are available from Robert Shaw, Inc. The flow adjustment valves FAV-1, FAV-2 may be commercially-available manual flow adjustment valves for operation at room temperature.

The three-way valve FSV-5 is used to facilitate the flow from either the open port or the closed port to reach the detector. Since the valve FSV-5 is in the pneumatic path of the vapor analyte, it needs to be heated to a 150-200 C temperature range, and a number of commercially-available gas sampling valves exist for operation in this temperature range. For example, the valve FSV-5 may be a three-way heated valve made by Parker instruments. All illustrated fluid couplings are swaplock SS rated couplings.

The MPMPTPS 2 is also equipped with three pumps P1-3. Pump P1 is dedicated for aerosol collection and solids-drying flow generation through the pyrolyzer inlet liner 12. This pump P1 must be powerful enough to generate 700 ml/min of air flow through the pyrolyzer inlet liner 12 with the filter in place. Pump P2 is used for filter 16 self-clean and regeneration option. The pump P2 should be able to drive a flow rate of at least 1000 ml/min through the pyrolyzer inlet liner 12 with the filter 16 installed. Pump P3 is used for initiating a split in the vapor analyte. This option is helpful if the analyte concentration exceeds the detector threshold. The magnitude of split flow rate is a user and application dependent parameter. All three pumps may be quaternary pumps from Millipore Co., Waters Division, Milford, Mass.

Open Port 4 Operations

The open port 4 is designed to work in two modes: Pyrolysis and Thermal Vaporization. Pyrolysis is useful for lysing high molecular weight substances, such as biological threat agents and very low vapor pressure chemical threat agents, so that transportable vaporous decomposition products of the analyte are generated that do not condense on the heated surfaces of the pneumatic pathway before arriving at the detector. The open port 4 is designed for at least twenty-four hours of uninterrupted aerosol monitoring. It features a filter self-clean option for prolonged non-serviced usage. This option is also used for continuous air monitoring for the presence of chemical threat agents. Also, direct liquid injection analysis of chemical and biological agents can be performed. The open port option is used for the following analyses.

Biological Sample Analysis

Biological agent challenge may be faced in the form of deliberate aerosol dissemination, contamination of water supplies and in solid powder form. To perform bio-aerosol analysis, ambient aerosol is concentrated and deposited on to the filter paper 16. A variety of commercially-available air-to-air aerosol concentrator's are available for this purpose. The aerosol concentrator minor flow output (the port on the aerosol concentrator from which the concentrated stream of aerosol particulates is extracted) is connected to the open port inlet (labeled as such) of the MPMPTPS 2. The open port inlet of the MPMPTPS and the minor flow output port of the aerosol concentrator should be lined up in a way that filter paper 16 is in a line of site with the minor flow output port of the aerosol concentrator. The liquid suspension (non-soluble biological sample suspended in a liquid matrix) can be directly deposited with the help of measured liquid injection. A powder form of a threat agent may be introduced using a spatula.

FIG. 2 is a sequential diagram illustrating the event sequence for performing the biological analysis, which includes sample collection, drying and pyrolysis:

Event #1 (Left) is the sample collection mode. For aerosol collection the pump P2 is switched on. The valve FSV-6 is left in the "normally closed" position to allow the flow through the pyrolyzer inlet liner 12 to pass. The valve FSV-4 is left in the "normally closed" position, which pneumatically connects the pyrolyzer inlet liner 12 to FSV-3. The valve FSV-3 is left in the "normally closed" position, which allows for unrestricted pneumatic access from pyrolyzer to the pump P2. The pump P2 pulls air flow through the pyrolyzer inlet liner 12 at a minimum to 500 ml/min. This flow in turn guides the minor flow from the aerosol concentrator to pass through the filter paper 16. The filter paper 16 traps the aerosol particles. This mode is used for user selectable periods of time to allow for a sufficient aerosol to be collected to meet the detector sensitivity requirements. For liquid and solid biological sample analysis, the aerosol collection step is bypassed. In the case of solid sample analysis, the solid sample is directly deposited onto the Filter paper 16 by using a spatula. Liquids in the form of suspensions and solutions may be introduced with the help of direct liquid injections to the open port inlet (labeled as such). No more than 5-μl aliquots should be introduced.

Event #2 (Center) is the drying mode. Immediately following the deposition of the biological sample, the collected sample is dried. An external fan used to cool the pyrolyzer (not shown in FIG. 2) is turned from normally on position to off. First, the valve FSV-3 is now switched from aerosol collection pathway to drying flow pathway. A flow adjustment valve, FAV-1, is set to allow a 10-15 ml/min of airflow to pass through the pyrolyzer inlet liner 12. The pyrolyzer coils 18 are supplied with 15 V-DC current for a period of two seconds. This raises the temperature of collected aerosol to about 130 C. Following the two-second heating period, the valves and pump settings are maintained for an additional eight to ten seconds. This ensures that the moisture and high vapor pressure volatile content in the aerosol is dried off. Now the sample is ready for pyrolysis analysis.

Event #3 (Right) is the pyrolysis mode. The valves FSV-3, 4 and 6 are left in the same mode as they were in event #2. A 15 VDC voltage is applied to the pyrolyzer coil 18 for a period of seven seconds. This event initiates pyrolysis. Approximately two to two and one half seconds into the pyrolysis event, the three way valve FSV-5 is switched from letting the carrier gas into the detector ("normally open" position) to pneumatically connect the pyrolyzer to the detector. The generated pyrolyzate or vaporous pyrolysis products are transported to the detector interface to be analyzed. The FSV-5 remains in this position until the end of the seven-second pyrolysis step. At the end of the pyrolysis step, pump P1 can either be switched off or remains on for collection of next batch of aerosol sample. Due to the inherent need for leaving the open port end connected to the aerosol concentrator in the case of aerosol analysis, a sub-ambient pressure detector is required to evacuate the generated analyte into the detector. The evacuation of analyte occurs because of the pressure gradient that exists between the detector and the open port pyrolyzer. If cyclical analysis of is desired, the external fan to cool the pyrolyzer is turned on and the analysis mode is returned to Event #1.

Filter Self-Clean and Regeneration

A continuous long-term and unattended aerosol analysis is a highly desirable tool to have in detection of a biological threat agent in aerosol form. In order to achieve this, a filter self-clean and regeneration process in required. A dirty filter 16 is undesirable for two reasons: first, the spent aerosol cake build-up reduces the airflow through the pyrolyzer 2 for aerosol collection and second, the spent aerosol cake may contain active carbon site, which may alter the pyrolyzate product chemistry, thus complicating the analysis. It is recommended that in an urban ambient aerosol monitoring mode, the filter paper 16 be cleaned every three hours of aerosol monitoring.

Figure 3:
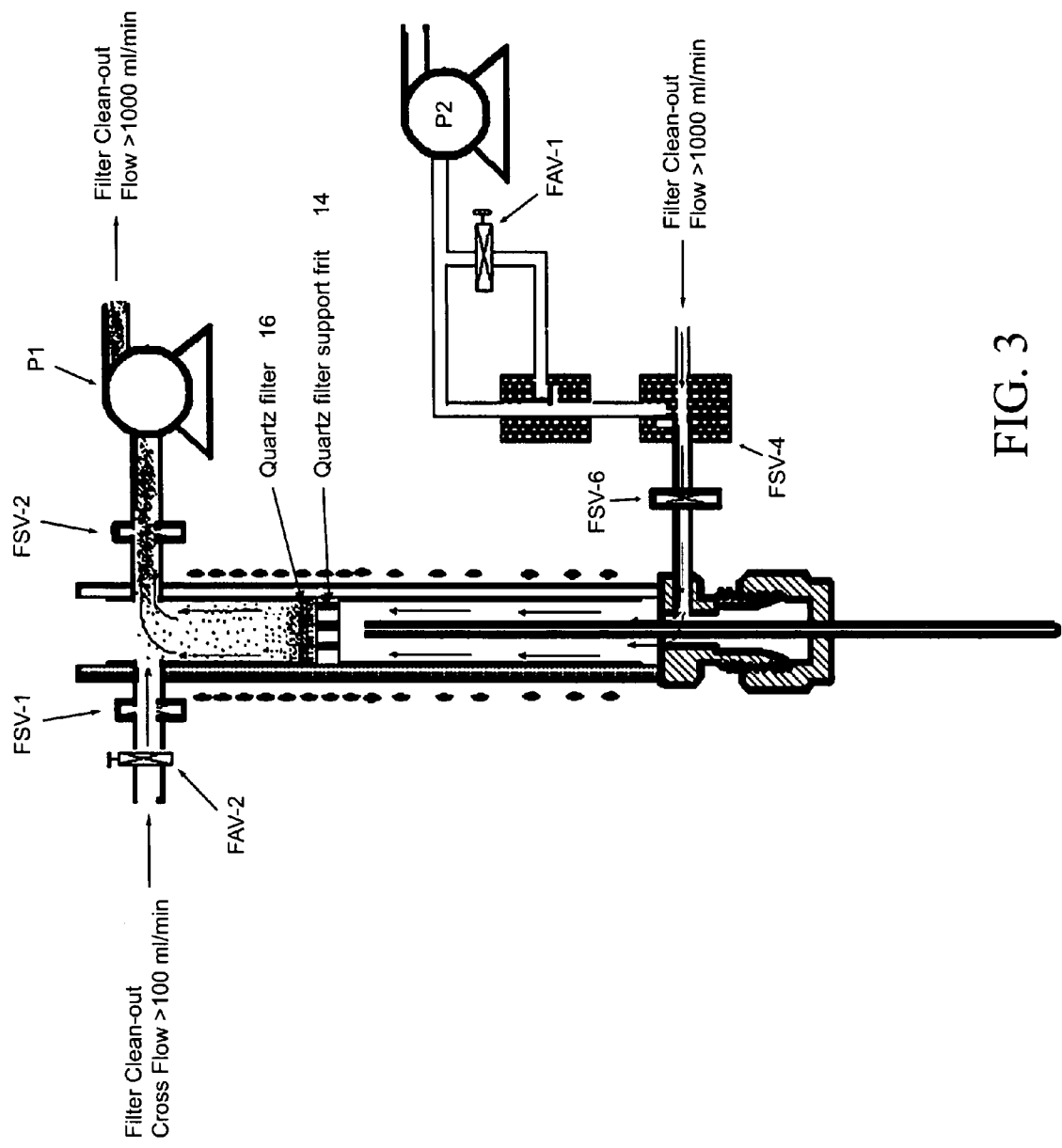
FIG. 3 is a schematic illustration of a set-up used for a self-clean option.

FIG. 3 is a schematic illustration of a set-up used for this self-clean option. The three way valve FSV-5 (not shown in FIG. 3, refer to FIG. 1) is set to open the closed port 6 to allow carrier gas flow to reach the detection. This pneumatically keeps the open port 4 disconnected from the detector. The pump P1 is switched on. The pump P1 needs to maintain a minimum 1000 ml/min of airflow. The flow adjustment valve FAV-1 is set to allow 100 ml/min of filter clean out cross flow. The valves FSV-1, FSV-2 and FSV-6 are switched to "open" positions from the "normally closed" positions. The valve FSV-4 is switched from allowing the aerosol collection to allowing the collected spent aerosol particulate fluidization flow or the filter clean-out flow. After this series of flow switching is accomplished, the pyrolyzer coil 18 is supplied with 15 V-DC current for ten seconds. This high heating allows for loosely bound spent aerosol particulates to re-suspend in the airflow sweeping through the pyrolyzer inlet liner 12. The cross-flow between the valves FSV-1 and FSV-2 removes the re-aerosolized spent particles from the pyrolyzer inlet liner 12. This procedure, thus, prolongs the usage of filter 16 to effectively trap the ambient aerosol for thermal analysis.

Chemical Vapor Analysis

Chemical threat agents may also be encountered in the vapor form. To analyze vapor (with reference to FIG. 1), the pyrolyzer cooling fan (not shown) is switched off. The flow switching valves, FSV-1 and FSV-2 are left at their "normally closed" positions, while the flow-switching valve FSV-6 is switched from the "normally open" to the "closed" setting. The pumps P1 and P2 are switched off. The pyrolyzer coils 18 are heated for about five seconds. Concurrent to the heating of the inlet liner 12, the flow switching valve FSV-5 is set to let the flow from the pyrolyzer to reach the detector, as opposed to let the carrier gas reach the detector. Under certain conditions, a splitting of the analyte may be required, when the sample amounts may be rendering the detector saturated. The flow switching valve FSV-7 could be set from the "normally closed" position to an "open position" and the pump P3 be switched on. The voltage applied to the pump P3 could be varied to set up a user-defined split of the analyte intake. This procedure allows for chemical vapor monitoring.

Chemical Liquid Analysis

The open-port 4 chemical liquid analysis should only be performed when the liquid sample contains high salt content or is visually turbid. If the liquid sample is a clear solution containing low concentrations of dissolved metal ion impurities, the closed port 6 option should be preferred because of better detection sensitivity limits obtained. The procedure for open port 4 analysis is very similar to that of chemical vapor analysis. To analyze the liquid sample, first a liquid sample is deposited in a measured aliquot of no more than a 2-µl liquid injection at the open port inlet. More than a 2-µl aliquot may not only be difficult to vaporize, but also, the vapor volume generated from vaporizing the liquid may well exceed the confines of the pyrolyzer inlet liner 12. The pyrolyzer cooling fan is switched off. The flow switching valves FSV-1 and FSV-2 are left at their "normally closed" positions. While the flow-switching valve FSV-6 is switched from the "normally open" to the "closed" setting. The pumps P1 and P2 are switched off. The pyrolyzer coils 18 are heated for about seven seconds. Concurrent to the heating of the pyrolyzer, the flow switching valve FSV-5 is set to let the flow from the pyrolyzer to reach the detector, while cutting off the carrier gas. Under certain conditions, a splitting of the analyte may be required, when the sample amounts may be rendering the detector saturated. The flow switching valve FSV-7 could be set from the "normally closed" position to the "open position" and the pump P3 could be switched on. The voltage applied to the pump P3 can be varied to set up a user-defined split of the analyte intake.

Modification to MPMPTPS System for Use with Positive Pressure Detectors

The MPMPTPS system 2 described in the above paragraphs is primarily designed for those detectors that function in sub-ambient pressures. A pneumatic pump can be used to evacuate the detector-analyzer to attain the sub-ambient pressure needed for optimum performance of the detector. The pressure gradient that exists between ambient atmosphere and the detector-analyzer serves as the driving force for moving the analyte either from the open-port 4 or the closed port 6 of the MPMPTPS 2. However, not all the chemical-vapor-detectors are at sub-ambient pressures. Due to critical design constraints and to reduce the size and power requirements of the detector, a few of these detectors require analyte to be "pushed into" the detector. These detectors are at ambient pressure. Thus, to hermetically seal the detector from any airleaks is not a priority. Therefore, even if desired and logistically possible, these detectors cannot be used at sub-ambient pressures. To be able to use the pyrolyzer in the open port 4 for biological agent detection in conjunction with any positive pressure or ambient pressure detector, a few critical modifications have to be made to the MPMPTPS 2. However, these modifications come at the expense of foregoing the bio-aerosol detection capability.

Figure 4:
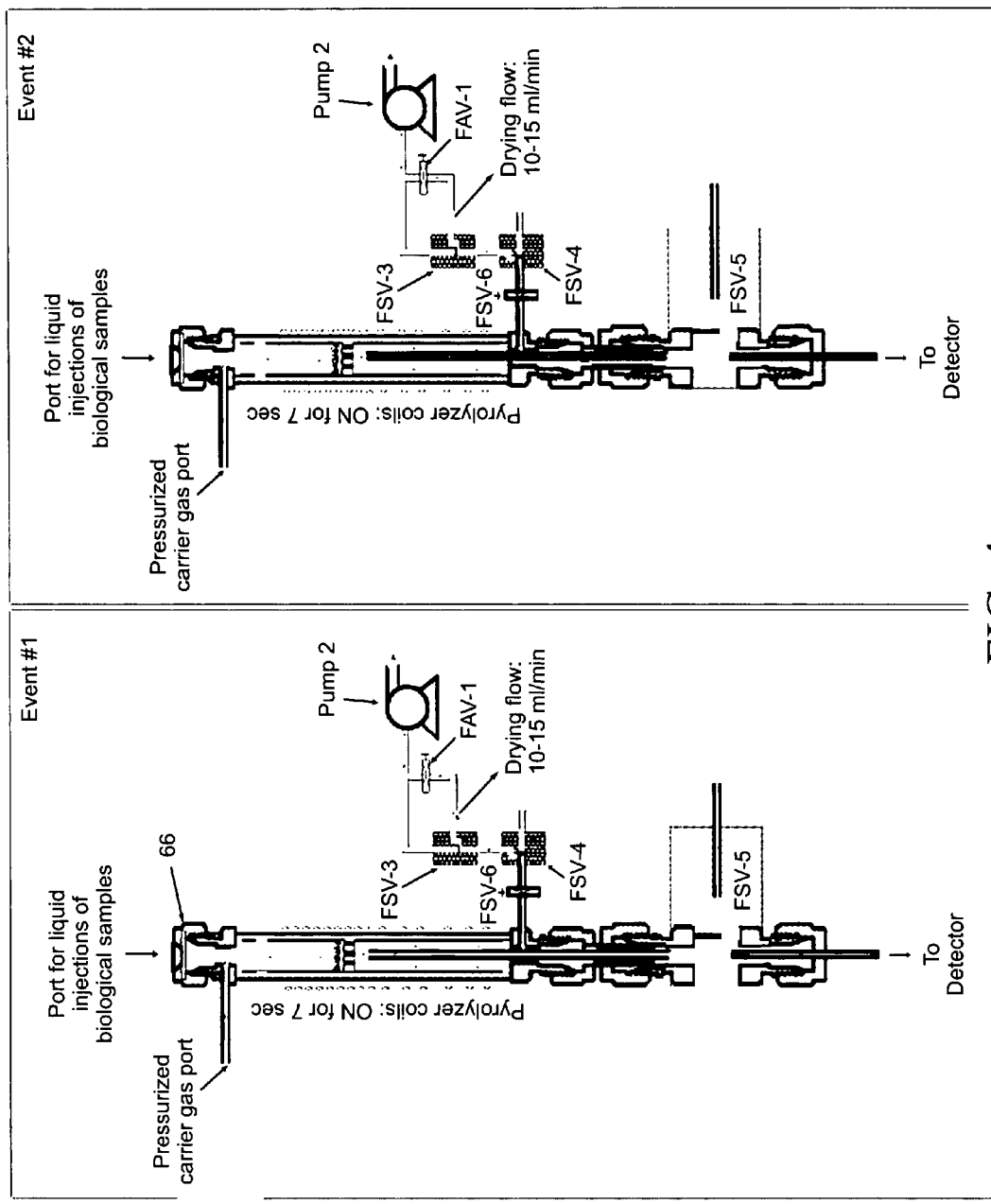
FIG. 4 shows an exemplary modification made to the MPMPTPS system 2 to adapt it to be used with ambient or positive pressure detectors.

FIG. 4 shows an exemplary modification made to the MPMPTPS system 2 to adapt it to be used with ambient or positive pressure detectors. These modifications are made only to the open port 4 part of the MPMPTPS (see FIG. 1). The closed-port option remains the same, with carrier gas supplied at a higher-than-detector pressure. The valves FSV-1 and 2 are removed. The open-port 4 is fitted with the same septum seal 66 as employed on the closed port, thus making the open-port 4 similar to closed port 6. The biological sample is deposited onto the quartz filter 16 in the form of a liquid suspension or solution with the help of a syringe. A solid sample is deposited on the filter 16 with the help of a spatula. The process of biological detection comprises of two events as described below, which include drying and pyrolysis:

Event #1 is the drying mode. Immediately following the deposition of the biological sample, the collected sample is dried. The external fan used to cool the pyrolyzer (not shown in the FIG. 5) is turned from a normally on position to off. First, the valve FSV-3 is switched to a drying flow pathway. A flow adjustment valve FAV-1 is set to allow 10-15 ml/min of airflow to pass through the pyrolyzer inlet liner 12. The pyrolyzer coils 18 are supplied with 15 VDC current for a period of two seconds. This raises the temperature of the collected aerosol to about 130 C. Following the two second heating period, the valves and pump settings are set for an additional eight to ten seconds. This ensures that the moisture and high vapor pressure volatile content in the aerosol is dried off. Now, the sample is ready for pyrolysis analysis. If chemical liquid analysis is desired, this event is skipped.

Event #2 is the pyrolysis mode. The valves FSV-3, FSV-4 and FSV-6 are left in the same mode as they were in event #1. A 15 V-DC voltage is applied to the pyrolyzer coil 18 for a period of seven seconds. This event initiates pyrolysis two to two and one-half seconds into the pyrolysis event, the three way valve, valve FSV-5 is switched from letting the carrier gas into the detector ("normally open" position) to pneumatically connect the pyrolyzer to the detector. The generated pyrolyzate or vaporous pyrolysis products are transported to the detector interface to be analyzed with the help of pressure gradient that exists between high-than-detector pressured carrier gas and the detector. The valve FSV-5 remains in this position until the end of the seven-second pyrolysis step. If chemical liquid analysis is desired, then the FSV-5 valve is switched concurrent to the onset of the pyrolysis step.

Closed Port 6

While the open port is useful for a biological analysis, chemicals in dirty liquid matrices and vapor form, it is not the best option to be used when analyzing chemical agents in clear and clean liquid matrices. The reason being that the open port is susceptible to losses of generated vapors to ambient air due to sudden thermal expansion. Also, the limit of a 2-μl aliquot injection limits the mass amount of analyte generated, especially for analysis with gas chromatograph systems. Also, the open port option cannot be used with solid phase microextraction (SPME). SPME devices, though selective, are highly useful for trace chemical agents analysis. The comparison of open port analysis, to closed port and SPME analysis is demonstrated by analysis of tri-butyl phosphate (TBP) dissolved in water.

FIG. 5 shows a comparative analysis of TBP. For this analysis, gas-chromatography-ion mobility spectrometer system (GC-IMS) was selected as the detector. From the figure, it is clear that the closed port liquid injections were five times better for TBP than for open port, while the SPME response was 200 times better than open port. The data strongly favors the use of closed port for chemicals in liquid analysis.

Referring back to FIG. 1, closed port analysis will now be described. The closed port heating profile is designed to facilitate flash vaporization of liquids that are injected into the deactivated gas chromatograph injection liner 62. The FSV-5 is set at the "normally open position" allowing carrier gas flow to reach the detection system. The sample is introduced either in the form of direct liquid injection (up to 10-μl aliquot, 5-μl aliquot preferred) or adsorbed on an SPME fiber 69. The SPME fiber 69 is a coated, fused-silica fiber, e.g., a needle like fibrous material (1-3 cm long and about 0.5 mm outer diameter) with a chemical coating of, for example, Carbowax/divinylbenzene. The coated chemical material absorbs the chemical analyte, either from vapor phase or by extracting it from liquid solutions. Upon heating the fiber, the fiber 69 releases the absorbed chemical analyte. The analyte is vaporized from liquid or from SPME fiber 69 due to the high temperature that the closed port is maintained at. The generated vapors are then transported to the detector, thus allowing for the chemical analysis.

It should now be apparent that the above-described system with its various modifications succeeds in pyrolyzing and/or vaporizing liquids in solution, suspension or colloidal form and solids to create an evolved vapor suitable for introduction into a variety of gas-chromatography and/or vapor detection systems, thereby allowing detection, classification and/or identification characteristics of threat agents. In conjunction with said detectors, the system makes it possible to provide a universal threat analysis system suitable for use with solids, aerosols, liquid solutions, liquid suspensions, liquid colloids, mists and vapors. Moreover, the system can be deployed as a fully-functioning field-able thermal analyses based sample-processing system for these multiple sample forms to increase versatility and market-based demand, especially for the purpose of chemical and biological threat assessment.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

We claim:

1. An apparatus for thermal analyses, comprising:

an open port pyrolyzation unit for generating pyrolyzate vapors from a sample;

a closed port split-less GC-injector interface unit for introducing clear liquids and solid-phase samples and generating vapors therefrom; and a three-way valve coupled to both said open port pyrolyzation unit and said closed port injector interface unit for selectively communicating the respective pyrolyzate vapors and injected vapors to a detector for analysis.

2. The apparatus for thermal analyses according to claim 1, wherein said detector is any one from among the group consisting of a negative, ambient or positive pressure detector.

* * * * *